(12) United States Patent
Klemm

(10) Patent No.: US 11,793,940 B2
(45) Date of Patent: Oct. 24, 2023

(54) CONTAINER FOR AN INJECTABLE MEDICAMENT

(71) Applicant: SANOFI, Paris (FR)

(72) Inventor: Thomas Klemm, Frankfurt am Main (DE)

(73) Assignee: SANOFI, Paris (FR)

( * ) Notice: Subject to any disclaimer, the term of this patent is extended or adjusted under 35 U.S.C. 154(b) by 469 days.

(21) Appl. No.: 16/964,694

(22) PCT Filed: Jan. 23, 2019

(86) PCT No.: PCT/EP2019/051553
§ 371 (c)(1),
(2) Date: Jul. 24, 2020

(87) PCT Pub. No.: WO2019/145318
PCT Pub. Date: Aug. 1, 2019

(65) Prior Publication Data
US 2021/0052817 A1    Feb. 25, 2021

(30) Foreign Application Priority Data
Jan. 26, 2018  (EP) .................................... 18305066

(51) Int. Cl.
*A61M 5/315*  (2006.01)

(52) U.S. Cl.
CPC . *A61M 5/31513* (2013.01); *A61M 2205/3306* (2013.01); *A61M 2205/3317* (2013.01);
(Continued)

(58) Field of Classification Search
CPC .. A61M 2205/3306; A61M 2205/3317; A61M 2205/3389
See application file for complete search history.

(56) References Cited

U.S. PATENT DOCUMENTS 4,355,899 A * 10/1982 Nussmeier ......... G01B 9/02003
356/498
4,380,394 A * 4/1983 Stowe ...................... G01B 9/02
356/482
(Continued)

FOREIGN PATENT DOCUMENTS

EP   17194273.3   *  9/2017  ............ A61M 5/315
JP   2000-186912      7/2000
(Continued)

OTHER PUBLICATIONS

PCT International Preliminary Report on Patentability in International Appln. No. PCT/EP2019/051553, dated Jul. 28, 2020, 7 pages.
(Continued)

*Primary Examiner* — Brandy S Lee
*Assistant Examiner* — John J Crawford
(74) *Attorney, Agent, or Firm* — Fish & Richardson P.C.

(57) ABSTRACT

A container for an injectable medicament can include an elongated body having a tubular-shaped sidewall extending along a longitudinal axis and having a distal end and a proximal end. The container can include an outlet at the distal end. The container can include a bung arranged inside the elongated body, sealingly engaged with the sidewall and slidable along the longitudinal axis relative to the sidewall. The container can include an interior volume to receive the injectable medicament and being confined by the sidewall, the outlet, and the bung. The container can include a measuring arrangement arranged in or on the bung. The measuring arrangement can include a signal generator configured to emit an electromagnetic measurement signal into or through the interior volume and a signal receiver configured to detect a feedback signal being indicative of an
(Continued)

interaction of the measurement signal with at least one of the sidewall, the outlet or the interior volume.

22 Claims, 3 Drawing Sheets

(52) U.S. Cl.
CPC .............. *A61M 2205/3389* (2013.01); *A61M 2205/3592* (2013.01); *A61M 2205/50* (2013.01)

(56) References Cited

U.S. PATENT DOCUMENTS

| | | | | |
|---|---|---|---|---|
| 9,719,772 | B2* | 8/2017 | Mansell | ............... G01B 9/0201 |
| 2015/0165114 | A1* | 6/2015 | Grant | ................ A61M 5/14248 |
| | | | | 604/151 |
| 2015/0174330 | A1 | 6/2015 | Nagel et al. | |
| 2016/0231229 | A1* | 8/2016 | Viitanen | ................. G01J 3/427 |
| 2017/0312430 | A1 | 11/2017 | Schleicher et al. | |
| 2017/0312455 | A1* | 11/2017 | Mirov | ............... A61M 5/31568 |
| 2019/0054252 | A1* | 2/2019 | Amschler | ............... A61M 5/24 |

FOREIGN PATENT DOCUMENTS

| | | |
|---|---|---|
| JP | 2015-505258 | 2/2015 |
| WO | WO 2007/024193 | 3/2007 |
| WO | WO 2013/096713 | 6/2013 |
| WO | WO 2014/009442 | 1/2014 |
| WO | WO 2014/067879 | 5/2014 |
| WO | WO 2014/145906 | 9/2014 |
| WO | WO 2015/109251 | 7/2015 |
| WO | WO 2016/140853 | 9/2016 |
| WO | WO 2017/040152 | 3/2017 |
| WO | WO 2017/155672 | 9/2017 |

OTHER PUBLICATIONS

PCT International Search Report and Written Opinion in International Appln. No. PCT/EP2019/051553, dated Mar. 27, 2019, 10 pages.

* cited by examiner

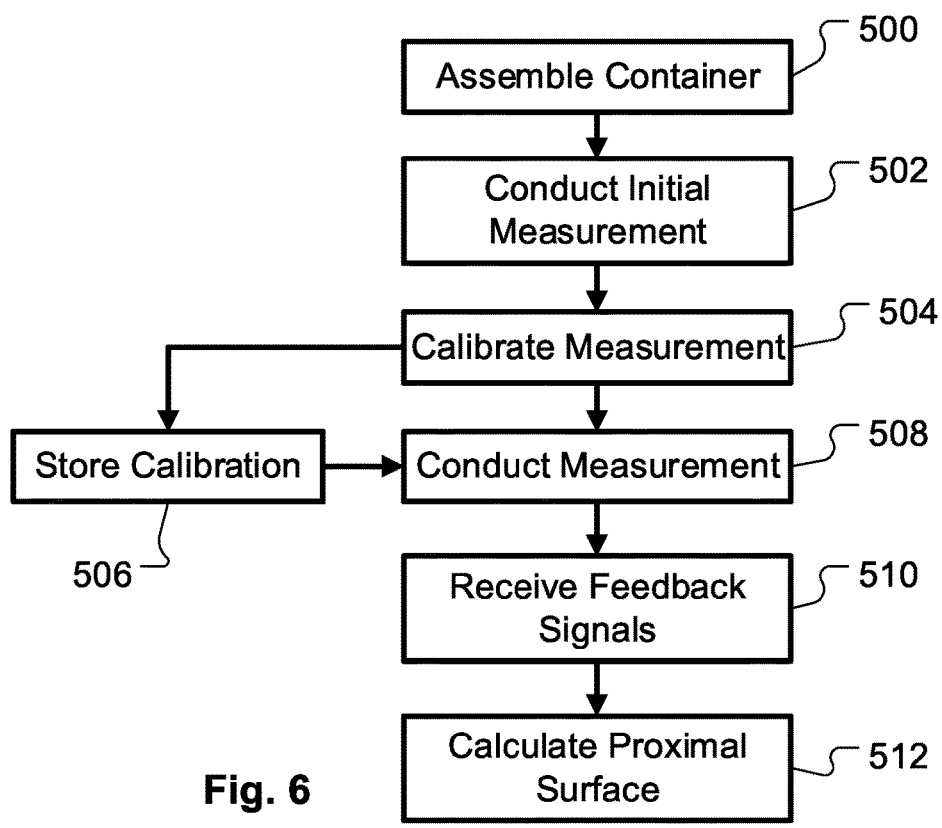
Fig. 6
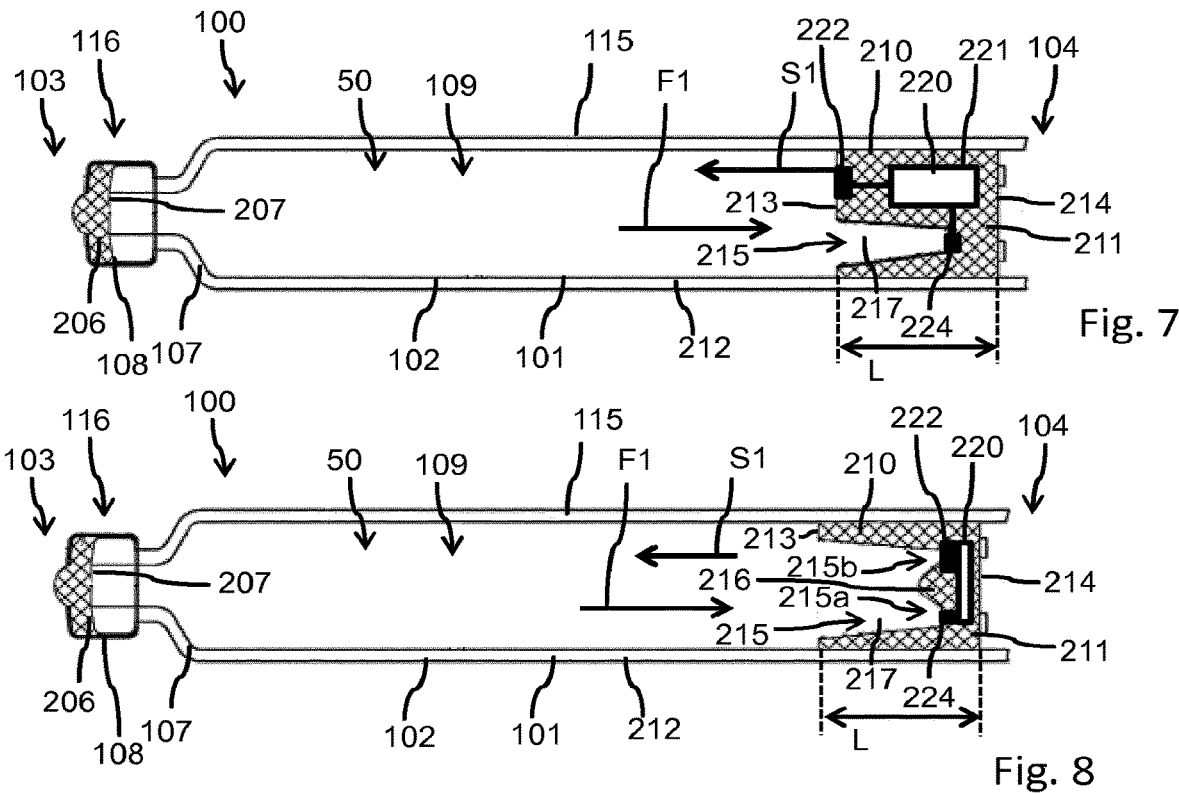
Fig. 7
Fig. 8

CONTAINER FOR AN INJECTABLE MEDICAMENT

CROSS REFERENCE TO RELATED APPLICATION

The present application is the national stage entry of International Patent Application No. PCT/EP2019/051553, filed on Jan. 23, 2019, and claims priority to Application No. EP 18305066.5, filed on Jan. 26, 2018, the disclosures of each of which are incorporated herein by reference in their entirety.

TECHNICAL FIELD

The present disclosure relates to measuring an interior volume of a container filled with a liquid substance, typically filled with an injectable medicament. The disclosure relates to a container for an injectable medicament. The container allows and supports a precise measurement of the size of an interior volume of the container occupied by the injectable medicament. The disclosure also relates to a method of determining the size of an interior volume of such a container.

BACKGROUND

Drug delivery devices for setting and dispensing a single or multiple doses of a liquid medicament are as such well-known in the art. Generally, such devices have substantially a similar purpose as that of an ordinary syringe.

Drug delivery devices, such as pen-type injectors have to meet a number of user-specific requirements. For instance, with patient's suffering chronic diseases, such like diabetes, the patient may be physically infirm and may also have impaired vision. Suitable drug delivery devices especially intended for home medication therefore need to be robust in construction and should be easy to use. Furthermore, manipulation and general handling of the device and its components should be intelligible and easy understandable. Such injection devices should provide setting and subsequent dispensing of a dose of a medicament of variable size. Moreover, a dose setting as well as a dose dispensing procedure must be easy to operate and has to be unambiguous.

Typically, such devices comprise a housing or a particular cartridge holder, adapted to receive a cartridge at least partially filled with the medicament to be dispensed. The device further comprises a drive mechanism, usually having a displaceable piston rod to operably engage with a bung or piston of the cartridge. By means of the drive mechanism and its piston rod, the bung or piston of the cartridge is displaceable in a distal or dispensing direction and may therefore expel a predefined amount of the medicament via a piercing assembly, e.g. in form of an injection needle, which is to be releasably coupled with a distal end section of the housing of the drug delivery device.

The medicament to be dispensed by the drug delivery device is provided and contained in a multi-dose cartridge. Such cartridges typically comprise a vitreous barrel sealed in distal direction by means of a pierceable seal and being further sealed in proximal direction by the piston. With reusable drug delivery devices an empty cartridge is replaceable by a filled one. In contrast to that, drug delivery devices of disposable type are to be entirely discarded when the medicament in the cartridge has been dispensed or used-up.

It is desirable to determine the amount of the medicament remaining in a cartridge while the cartridge is arranged inside a drug delivery device. It is also desirable to determine an interior volume of the cartridge occupied by the liquid injectable medicament. Determination of measurement of the interior volume should be rather precise, reliable and highly reproducible. It is desirable to provide a container for injectable medicament readily equipped with volumetric measurement means that enables and supports electronic data processing.

SUMMARY

The present disclosure provides a container for an injectable medicament. The container comprises an elongated body having a tubular-shaped sidewall extending along a longitudinal axis (z) and having a distal end and a proximal end. The distal end is located opposite to the proximal end. The container further comprises an outlet at the distal end of the elongated body. The container further comprises a bung or a piston arranged inside the elongated body. The bung is sealingly engaged with the sidewall and is slidable along the longitudinal axis relative to the sidewall. The container further comprises an interior volume that may be also denoted as a filling volume. The interior volume or filling volume is configured to receive and to contain the injectable medicament. The interior volume is confined by the sidewall, by the outlet and by the bung.

The container further comprises a measuring arrangement that is arranged in or on the bung. The measuring arrangement comprises a signal generator that is configured to emit a measurement signal into or through the interior volume. The measuring arrangement further comprises a signal receiver configured to detect a feedback signal that is indicative of an interaction of the measurement signal with at least one of the sidewall, the outlet or the interior volume. If the container and hence the interior volume is occupied or at least partially filled with the injectable medicament the feedback signal may be further indicative of an interaction of the measurement signal with the liquid medicament contained in the interior volume.

With the measuring arrangement in or on the bung a container with an integrated measuring arrangement is provided. The bung of the container may be readily equipped with the measuring arrangement. The signal generator and the signal receiver of the measuring arrangement are configured to conduct a measurement by emitting measurement signals and by detecting feedback signals in return. The measurement signal and its interaction with at least one of the sidewall, the outlet, the interior volume or the injectable medicament leads to the generation of a detectable feedback signal. The detection of the feedback signal allows to derive at least one physical or chemical parameter of the container. In particular, the feedback signal obtainable and detectable by the signal receiver is processable to determine at least one of the size of the interior volume and the longitudinal position of the bung relative to the sidewall of the body of the container.

The integration of the signal generator and the signal receiver into or on the bung makes a separate attachment and arrangement of signal generator and signal receiver to the container superfluous. In order to provide a volumetric measurement of the interior or inside volume of the container it may be sufficient to provide the container with a particular bung as described above being equipped at least with a signal generator and a signal receiver.

At least one of the signal generator and the signal receiver or both, the signal generator and the signal receiver may be located entirely inside the volume or inside the bulk of the bung. The signal generator and/or the signal receiver may be entirely enclosed by the bung. With other examples at least one of the signal generator and the signal receiver may be arranged at least partially inside the bung. A portion of at least one of the signal generator and the signal receiver may flush with an outside surface of the bung. With other examples at least a portion of at least one of the signal generator and the signal receiver may protrude from an outside surface of the bung, e.g. from a distal face of the bung. Since the signal generator is configured to emit a measurement signal into or through the interior volume the signal generator may be located near a distal face of the bung pointing towards the distally located outlet of the container. Also, the signal receiver may be located at or close to the distal face of the bung so as to have immediate access to the interior volume.

With examples wherein at least one of the signal generator and the signal receiver are entirely enclosed or embedded inside the bung either the measurement signal or the feedback signal may be configured to propagate through the bung. If the signal generator is located inside the bung at a non-zero distance from both, a distal end face and a proximal end face of the bung the measurement signal generated by the signal generator propagates through the bung and into the interior volume confined by the bung. If the signal receiver is entirely embedded inside the bung at a non-zero distance from both, the distal end face and the proximal end face of the bung the feedback signal may also propagate from the interior volume into the bung in order to become detected by the signal receiver.

By having the signal generator and the signal receiver attached to or entirely located inside the bung even existing containers, such as cartridges for injectable medicaments and their elongated bodies can be retrofitted with a measuring arrangement. Here, an existing bung, typically configured as a rubber stopper can be exchanged by a bung as described above, which bung is equipped with the measuring arrangement.

Typically, the bung comprises an elastomeric material, such as natural or synthetic rubber. The bung may comprise a cyclic olefin polymer (COP) and/or a cyclic olefin copolymer. The bung may also comprise a polymer material on the basis of EPDM ethylene propylene diene monomer rubber. The measuring arrangement may be encapsulated inside the bung. The measuring arrangement may comprise a hermetic housing configured to accommodate at least the signal generator and the signal receiver. The housing may be embedded inside the bulk of the bung. The encapsulation of at least the signal generator and the signal receiver inside the house of the measuring arrangement enables a multitude of different ways to manufacture the bung. For example, the housing with the signal generator and the signal receiver located therein may be subject to an over-molding by a bung-forming material.

With other examples the bung may comprise at least two bung components that are configured to become mechanically assembled together to form the bung. Here, the measuring arrangement can be arranged between these bung components in order to embed the measuring arrangement inside the bung.

By embedding the measuring arrangement inside the bung the measuring arrangement is inherently protected against environmental influences or hazards. Moreover, the measuring arrangement can be concealed by and inside the bung. The embedding of the measuring arrangement inside the bung may have no influence on the outside geometry of the bung. If the measuring arrangement is entirely embedded inside the bung and hence enclosed by the bung it is not visible from outside. In this way, the measuring capability of the container can be effectively concealed. This may enable a concealed supervision or monitoring of the filling level of the container.

According to a further example the container comprises a processor connected to the signal receiver. The processor may be arranged inside the bung. The processor may belong to the measuring arrangement. Hence, the measuring arrangement may comprise the processor. The processor is configured to process signals obtainable from the signal receiver when receiving at least one feedback signal. The signal receiver is typically configured to generate an electrical signal in response to receive a feedback signal. An electrically conductive connection between the processor and the signal receiver enables a respective signal processing. Based on the signals obtainable from the signal receiver the processor is configured to determine at least one of a size of the interior volume or the longitudinal position of the bung relative to the body of the container.

The processor may comprise an integrated circuit, such as an application specific integrated circuit (ASIC). The processor may be implemented as a microcontroller. The processor is at least electrically connected to the signal receiver. The processor may be also located inside the bung. Typically, the processor is located on a printed circuit board (PCB). At least one of the signal generator and the signal receiver may be located and integrated on the same PCB. The entire measuring arrangement may be configured or implemented as an ASIC and may be provided on a single common PCB. With other examples the processor may be located outside the measuring arrangement. The processor may be located on a proximal surface of the bung. It may be also located outside the bung or at a predefined non-zero distance from the bung.

The processor may be located even outside the container. The connection between the processor and the signal receiver may be of wired or wireless type. When the processor is located inside or on the bung there is provided a wired connection between the processor and the signal receiver. With examples wherein the processor is located outside the bung and/or outside the container the processor may be connected to the signal receiver in a wireless way.

In a further example the processor is configured to determine a size of the interior volume on the basis of the feedback signal obtainable through the signal receiver. For this, the processor may be configured to determine a magnitude or amplitude of the feedback signal. The processor may be configured to determine a time or time delay at which the feedback signal is detected compared to a reference signal. Alternatively, the processor may be configured to determine a phase shift between a feedback signal and a reference signal. The processor may be further configured to compare a feedback signal with a predefined signal or with a previously detected feedback signal. In this way, the processor may be configured to monitor and to process a temporal variation of the feedback signal or of a series of feedback signals. A temporary variation of the feedback signal may be indicative of the size of the interior volume and/or of the longitudinal position of the bung.

With a further example the processor is connected to the signal generator. Typically, the processor is connected to both, the signal generator and to the signal receiver. Here, the processor is configured to trigger the emission of the measurement signal. The processor is further configured to determine the size of the interior volume on the basis of a comparison of at least one measurement signal with at least one feedback signal. The processor may be further configured to conduct a comparison of at least one measurement signal with several feedback signals. Alternatively or additionally the processor may be configured to compare at least one feedback signal with several measurement signals. Moreover, the processor may be configured to compare a multitude of measurement signals with a multitude of feedback signals.

The signal generator may be configured to emit a series or a sequence of measurement signals. Accordingly, the signal receiver may be configured to detect a respective series or sequence of measurement signals in return. Here, the processor may be configured to conduct a mutual comparison of feedback signals of a sequence of feedback signals. In this way, temporal fluctuations of the feedback signal or of the feedback signals can be detected. Such a temporal fluctuation may be indicative of the size of the interior volume and/or of the longitudinal position of the bung relative to the body of the container.

Moreover, since the processor is connected to both, the signal generator and to the signal receiver the processor may be configured to measure a time delay between the emission of a measurement signal by the signal generator and the detection of a feedback signal by the signal receiver. From a determination of such a time delay the size of the interior volume and/or the longitudinal position of the bung may be precisely determined. In addition or as an alternative, the processor may be configured to compare the magnitude or amplitude of the feedback signal with a given reference amplitude. The amplitude or magnitude of the measurement signal may be directly indicative of the size of the interior volume and/or of the longitudinal position of the bung relative to the body.

In another example the measuring arrangement comprises a data storage configured to store at least one of an initial size of the interior volume and at least one feedback signal. The data storage may be configured to store an initial size of the interior volume or at least one feedback signal during a calibration procedure of the container. It is conceivable, that upon or after filling the container with the injectable medicament the measuring arrangement is triggered to conduct a measurement, i.e. to emit a measurement signal and to detect a feedback signal in return.

Such an initial measurement may enable a calibration of the container. In such an initial measurement procedure the interior volume derived by the processor and/or the feedback signal may be stored as a reference volume or as a reference signal in the data storage. For subsequent measurement procedures the volume derived or determined by the processor and/or the feedback signal obtainable through the signal receiver may be compared to the reference volume and/or to the reference signal previously stored in the data storage. The processor may be configured to conduct a quantitative comparison between a feedback signal and the reference feedback signal previously stored in the data storage. From the size or magnitude of a feedback signal in comparison to the size or magnitude of the reference feedback signal the size of the interior volume and/or the longitudinal position of the bung may be derived directly.

The data storage is typically connected to the processor. It may be also connected to at least one of the signal generator and the signal receiver. The connection between the processor and the data storage allows for comparing an actually detected feedback signal with a previously detected feedback signal. The data storage may comprise a buffer for a sequence of feedback signals. The signal receiver may be configured to fill the buffer of the data storage as a sequence or series of feedback signals is detected by the signal receiver. The buffer of the data storage and the sequence of feedback signals stored therein may become subject to a stepwise data processing. The data storage therefore enables a reduction of the demands to the processor in terms of computational power. The electric energy consumption of the processor and of the entire measuring arrangement may be decreased by making use of the data storage. The data storage is typically integrated into the integrated circuit of the measuring arrangement. It may be located on a common PCB of the measuring arrangement. The processor and the data storage may be located and arranged on a common PCB.

In a further example the container comprises a communication interface configured to exchange data with an external electronic device. The communication interface may be located inside the bung. It may belong to the measuring arrangement. Hence, the measuring arrangement may comprise the communication interface. The communication interface member located inside or outside a housing of the measuring arrangement. The communication interface may comprise a wireless communication interface. In a further example the communication interface is a wired communication interface. The communication interface is typically connected to the processor and/or to the data storage. The communication interface may be also directly or indirectly connected to at least one of the signal generator and the signal receiver. The communication interface may be connected to both, the signal generator and to the signal receiver. Typically, the communication interface is located inside the bung. The communication interface and the processor are connected through a wired connection.

In one example, the measuring arrangement may be located or encapsulated inside the bung while the communication interface is located on an outside surface of the bung, e.g. on the proximal face of the bung. The communication interface may be also integrated into the measuring arrangement. The communication interface may be located inside the housing of the measuring arrangement. The communication interface may be integrated into the integrated circuit of the measuring arrangement. The communication interface, the processor and the storage may be arranged on a common PCB.

The communication interface is configured to communicate with an external electronic device. The communication interface may be configured to communicate with the external electronic device in accordance to a well-defined communication standard or communication protocol, such as WIFI, Bluetooth, NFC or other radio frequency-based communication standards. The communication interface may be configured to exchange data with the external electronic device, such as data obtained and generated by the processor. The external electronic device may be a portable electronic device, such as a smartphone or a tablet computer.

The data exchange between the communication interface and the external electronic device may comprise unprocessed feedback signals detected by the signal receiver and transmitted via the communication interface to the external electronic device. With such an example it is generally conceivable that it is the external electronic device that comprises a processor configured to process feedback signals detected by the signal receiver and transmitted to the external electronic device via the communication interface. In this way, electric power consumption of the container and hence of the measuring arrangement may be reduced. Moreover, the processor can be provided outside and remote from the container. Manufacturing costs for the container and for the measuring arrangement integrated in the bung may be thus reduced.

According to a further example the container comprises an antenna configured to withdraw electric energy from a surrounding electromagnetic field. It may be the measuring arrangement that comprises the antenna. The antenna may be arranged in or on the bung of the container. Typically, the antenna is electrically connected to the processor. The antenna may be further directly electrically connected to the communication interface. The antenna may be integrated into the communication interface or vice versa, i.e. the communication interface may be integrated into the antenna. It is conceivable that the communication interface communicates with the external electronic device via the antenna.

The antenna may therefore provide a twofold functionality. It may enable data exchange with an external electronic device. Moreover, the antenna is configured to withdraw electric energy from a surrounding electromagnetic field. The antenna may therefore provide and supply the measuring arrangement with electrical energy obtainable from a surrounding electromagnetic field. The antenna may comprise a NFC antenna. The electric energy necessary to drive or to power the measuring arrangement may be exclusively provided by the antenna and may be exclusively withdrawn from a surrounding electromagnetic field. Alternatively or additionally the measuring arrangement may be equipped with an electric energy storage, such as a battery. In a further example the measuring arrangement and hence the bung may be connectable to an external source of electric energy. For instance, when assembled inside an injection device the bung may be brought in electrical contact with an electric energy source.

In a further example the measuring arrangement comprises an electric energy storage that is connected to the antenna. In this way, the antenna is configured to charge the electric energy storage. In situations where a surrounding electromagnetic field is absent the electric energy storage may provide sufficient electric energy to drive or to power the measuring arrangement. The electric energy storage is typically connected to the measuring arrangement. It is connected to the signal generator in order to generate and to emit a measurement signal.

The electric energy storage is also connected to the signal receiver in order to enable detection of a feedback signal. The electric energy storage is connected to the processor in order to enable a processing of detected feedback signals. The electric energy storage may be further connected to the data storage. In this way, reading of data from the storage as well as writing data into the data storage becomes enabled. The electric energy storage is further connected to the communication interface so as to enable data exchange or data transmission to an external electronic device.

According to another example the signal generator comprises a light source configured to emit an optical measurement signal towards the outlet. Here, the signal generator may be configured as a light source. The signal generator may comprise a light emitting diode (LED) configured to emit an optical signal, e.g. a light beam or a light pulse of a predetermined frequency or predetermined spectral range or spectral width. The optical measurement signal generated and emitted by the optical signal generator may be in the visible spectrum or in the invisible spectrum. The optical measurement signal may comprise a frequency in the infrared spectrum or in the ultraviolet spectral range. When the signal generator is configured to generate and to emit an optical measurement signal in the non-visible range the emission of the optical measurement signal is not perceivable by users of the container. Hence, the capability and functionality of the measuring arrangement can be effectively concealed and the user of the container will not be distracted or confused when the optical signal generator emits an optical measurement signal.

The optical signal generator may be configured to emit a collimated light beam or a collimated light pulse into the interior volume of the container. The measurement signal in form of an optical measurement signal propagates through at least a portion of the interior volume. The feedback signal is also an optical feedback signal. For instance, the optical measurement signal may be subject to a reflection, e.g. at the sidewall of the body of the container and/or at the outlet. The optical feedback signal may be an optical measurement signal reflected by at least one of the outlet and the sidewall.

The signal receiver typically comprises a light detector, such as a charge coupled light detector. The signal receiver may comprise a photodiode or a charge coupled device (CCD). The signal receiver may be configured to quantitatively determine the magnitude of the optical feedback signal. Depending on the transmissivity of the interior volume and the injectable medicament located therein the decrease in intensity of the optical feedback signal compared to the intensity of the optical measurement signal may be directly indicative of the optical path length, the optical measurement signal and the optical feedback signal propagating through the interior volume.

The attenuation of the intensity of the optical feedback signal compared to the optical measurement signal may be a direct indication for the optical path length between the signal generator, a particular portion of the sidewall or the outlet and the signal receiver. As the bung is subject to a distally directed sliding motion the optical path length between the signal generator and the signal receiver is constantly reduced thus leading to an increase of the intensity of the optical feedback signal. The variations in intensity of the optical feedback signal are therefore a direct indication for the longitudinal displacement of the bung relative to the sidewall of the container.

With another example the signal receiver comprises a time of flight detector (TOF) or a TOF camera that is configured to detect the optical measurement signal reflected from the outlet as the optical feedback signal. A time of flight detector is configured to measure a time interval required for a light pulse to propagate from the signal generator towards the outlet and back from the outlet to the signal receiver. The time of flight measuring depends on the finiteness of the speed of light and the ability to measure the TOF either directly with clocks or indirectly by, for example, comparing the phase of an emitted light beam or light pulse with the phase of the reflected light beam or light pulse.

In another example the signal generator is configured to generate and to emit at least one or several light pulses into the interior volume at a first point of time $t1$ and the signal receiver is configured to detect at least one or several reflected light pulses. The signal receiver is typically configured to detect light pulses previously emitted by the signal generator and reflected by at least one of the sidewall, the outlet and the proximal surface of the pierceable seal. The signal receiver is configured to detect or to determine a second point of time $t2$ at which reflected light pulses are detected. A time interval between the first point of time $t1$ and the second point of time $t2$ is indicative of a time delay required by the emitted light to propagate from the signal generator to the signal receiver. At least one of the processor and the signal receiver is configured to determine or to measure such a time delay being indicative of the optical path length between the signal generator and the signal receiver. From this, the distance between the bung and an optically reflective structure, e.g. the proximal surface of the pierceable seal, can be precisely determined. Typically, both the signal generator and the signal receiver are connected to the processor and are driven or triggered by the processor.

With the knowledge of the speed of light of approximately 300,000 km/s the optical path length between the signal generator, the outlet and the signal receiver can be precisely determined. The measurement or distance resolution of the TOF measuring arrangement comprising a TOF sensor may be less than 1 cm, less than 5 mm or less than 1 mm. The knowledge of the relative position of the signal generator and the signal receiver and knowledge of the index of refraction of the interior volume and/or the injectable medicament located therein allows to derive and to precisely determine the geometric distance between the bung and the outlet thus enabling to calculate the size of the interior volume and hence of the momentary filling level of the container.

In one example of operation the optical signal generator and the optical signal receiver in its implementation as a time of flight detector are configured to generate and to emit several light pulses. As an alternative to the measurement of a time delay also a phase shift between the light beams emitted by the optical signal generator and the reflected light beams detected by the optical signal receiver can be compared, e.g. by the processor. The time of flight and hence the optical path length as well as the geometric path length can then be derived from a phase shift between the emitted light pulses and the detected light pulses.

With a TOF implementation the processor triggers the optical signal generator to emit at least one or a sequence of light pulses propagating into and through the interior volume as optical measurement signals. Optical feedback signals provided by a reflection of the optical measurement signals, e.g. at the inside face or proximal face of the outlet, are detected by the time of flight sensor. The time delay between the emission of the optical measurement signal by the signal generator and the detection of the optical feedback signal by the signal receiver is typically measured by a clock According to a further example the measuring arrangement comprises an optical interferometer configured to determine a distance between the outlet and the bung on the basis of an optical phase shift between the optical feedback signal and a reference optical signal. The optical interferometer may be of Mach-Zehnder type or Michelson type. It may comprise a beam splitter and at least two reflectors, e.g. in form of mirrors. The optical interferometer typically comprises a reference path and a signal path. A light beam emitted by a light source is split into a signal beam and a reference beam.

The reference beam is directed towards a reflector. The distance between the reflector and the respective beam splitter is constant. The signal beam propagates from the beam splitter to an object. It is reflected by the object and at least a portion thereof returns to the beam splitter. At the beam splitter, the reference beam reflected from the reference reflector and the signal beam reflected from the object recombine and interfere. The light source and the light beam emitted by the light source comprises a coherence length that is at least half of the distance of a total axial displacement path of the bung relative to the body of the container. The optical interferometer may be configured to have a signal path and a reference path of equal length when the bung is about halfway between a proximal end position and a distal end position.

As the reflected reference beam and the reflected signal beam are recombined an interference pattern is generated at the optical signal receiver. As the bung is subject to a longitudinal movement, the distance between the beam splitter and the object is subject to a variation thus leading to a quantitative modification of the interference pattern on the optical signal receiver. The optical signal receiver typically comprises a charge coupled device. The charge coupled device comprises a linear and hence one-dimensional array or a two-dimensional array of charge coupled detectors or pixels. The pattern obtained at the optical signal receiver may be processed by the processor.

Alternatively, the pattern detected at the optical signal receiver may be processed by the external electronic device.

For this, the communication interface may be configured to transmit the pattern of the optical signal receiver to the external electronic device for further processing. An optical interferometer provides a rather precise position and displacement measurement of the bung relative to the body of the cartridge.

In another example the optical interferometer may be at least partially fiber implemented. For instance, the reference path may be provided by an optical fiber. Here, the optical interferometer comprises an optical fiber forming the reference path for the optical reference signal. A free end of the optical fiber may comprise a reflective end. Moreover, the fiber can be coiled inside the bung so as to reduce the space required for the measuring arrangement. The optical interferometer may be configured to direct the signal beam towards the outlet. The outlet may comprise a reflective surface, e.g. in form of a proximal surface of a pierceable membrane that is provided on the outlet.

Interferometry relies on the wave nature of light and the ability of waves to interfere. The signal receiver is typically connected to the signal generator. Typically, the processor is connected to both, the signal generator and the signal receiver.

Generally, and for any of the examples as described herein the optical signal generator as well as the optical signal receiver can be integrated on a chip or printed circuit board thus allowing a further miniaturization of the size of the measuring arrangement.

When the measuring arrangement is optically implemented, i.e. when the signal generator is an optical signal generator and when the signal receiver is an optical signal receiver the bung may comprise a translucent material. Here, at least one of the optical signal generator and the optical signal receiver may be located inside the bung at a predetermined non-zero distance from an end face or circumference of the bung. With other examples at least one of the signal generator and the signal receiver may be located at a distal end face of the bung. At least one of the optical signal generator and the optical signal receiver may flush with the distal face of the bung. In other examples both, the signal generator and the signal receiver are located at the distal end face of the bung or flush with the distal end face of the bung.

According to another example at least one of the optical signal generator and the optical signal receiver is arranged in a recess of a distal face of the bung. For instance, the optical signal generator is arranged in the recess. In this way, the propagation characteristics of the optical signal generated and emitted by the optical signal generator can be influenced. Typically, the optical signal generator is arranged in a recess of a distal face of the bung while the optical signal receiver is arranged at the distal face of the bung. Hence, the optical signal generator and the optical signal receiver are arranged at a predefined longitudinal offset from each other. The optical signal generator and the optical signal receiver may be also offset in radial or circumferential direction. By arranging the optical signal generator in a recess optical measurement signals emitted by the optical signal generator are hindered from impinging the optical signal receiver directly. Insofar the recess forms a kind of a screen for the optical signal receiver.

In another example it is the optical signal receiver that is arranged in a recess of the distal face of the bung and the optical signal generator is arranged at the distal face of the bung. In this way, it is the optical signal receiver that is screened by the recessed arrangement of one of the optical signal generator and the optical signal receiver at the distal face of the bung. This provides the benefit that only light beams or light pulses reflected from the outlet can be detected by the optical signal receiver.

The recessed arrangement of at least one of the optical signal generator and the optical signal receiver in the distal face of the bung is of further benefit when the bung is positioned rather close to the outlet of the container. If the container is almost empty and if the interior volume approaches a minimum size the distance between the distal face of the bung and the outlet will approach a minimum. With a recessed arrangement of at least one of the optical signal generator and the optical signal receiver the optical path length between the optical signal generator, the outlet and the optical signal receiver can be slightly increased compared to the geometric distance between the outlet and the distal face of the bung. This may be beneficial for enabling a time of flight-based distance determination even for small distances between the outlet and the bung.

According to another aspect the disclosure further relates to a method of determining the size of an interior volume of a container as described above. The method comprises the steps of generating and emitting a measurement signal from the measuring arrangement into or through the interior volume of the container. Thereafter, at least one feedback signal is detected, typically by the signal receiver. The detected feedback signal is indicative of an interaction of the measurement signal with at least one of the sidewall, the outlet or the interior volume of the container. Thereafter and in a final step the size of the interior volume is determined on the basis of the feedback signal. Typically, the method is conducted by a processor located inside the bung or provided outside the bung. The processor may be integrated into the measuring arrangement. With other examples the processor may be located in an external electronic device. Here, the measuring arrangement may be equipped with a communication interface configured to transmit or to exchange data with the external electronic device. The communication interface is then connected to at least one of the signal generator and the signal receiver. It may be connected to both, the signal generator and the signal receiver.

Generally speaking, the method of determining the size of an interior volume of the container is conducted by means of the container as described above. Accordingly, any features, benefits and modes of operation described above in connection with the container equally apply to the method of determining the size of the interior volume of the container; and vice versa.

In the present context the term 'distal' or 'distal end' relates to an end of the injection device that faces towards an injection site of a person or of an animal. The term 'proximal' or 'proximal end' relates to an opposite end of the injection device, which is furthest away from an injection site of a person or of an animal.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39), des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains p and E have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystallizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present invention without departing from the spirit and scope of the invention. Further, it is to be noted, that any reference numerals used in the appended claims are not to be construed as limiting the scope of the invention.

In the following, numerous examples of the container and of an injection device will be described in greater detail by making reference to the drawings, in which:

BRIEF DESCRIPTION OF FIGURES

FIG. 6 shows a flowchart of a method of determining the size of an interior volume of the container, FIG. 7 shows a longitudinal cross-section through another example of the container, and FIG. 8 is illustrative of a further example of a container.

DETAILED DESCRIPTION

Figure 1:
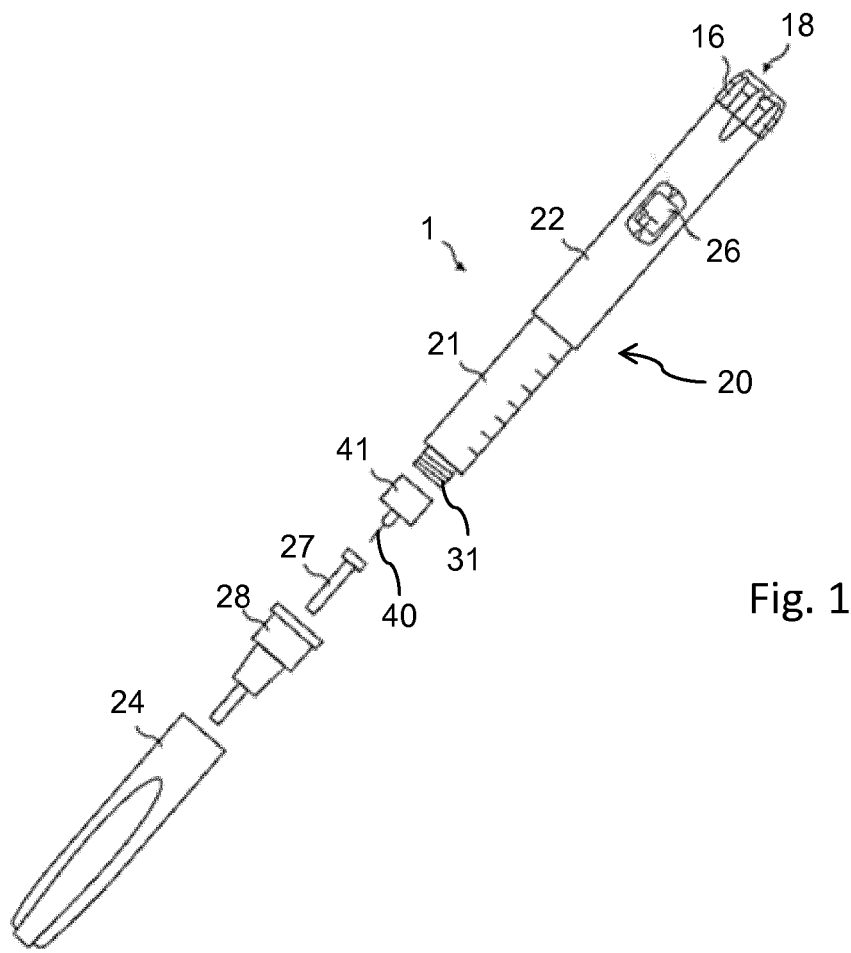
FIG. 1 shows an example of an injection device.
Figure 2:
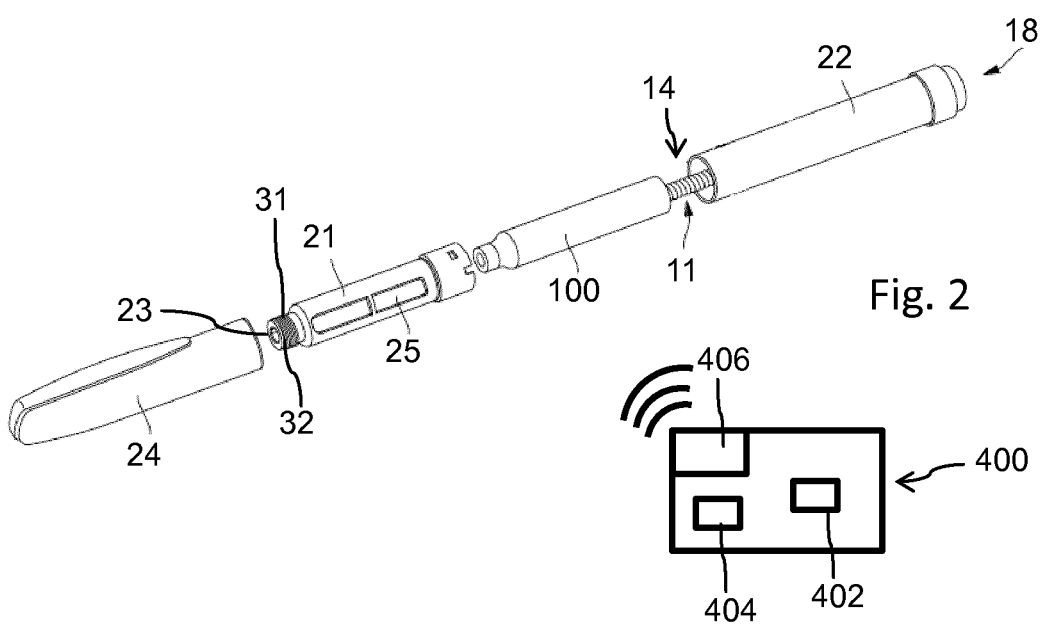
FIG. 2 shows the injection device partially disassembled and equipped with a container filled with an injectable medicament.

In FIGS. 1-2 an example of an injection device 1 configured as a pen type injector is illustrated. The injection device 1 comprises a housing 20. The housing 20 comprises a cartridge holder 21 and a body 22. The cartridge holder 21 is configured to accommodate a container 100 that may comprise a cartridge that is prefilled with at least a first injectable medicament 50. The cartridge holder 21 and the body 22 may be permanently or releasably attached to each other. With a permanent or non-releasable connection of cartridge holder 21 and body 22 the injection device 1 may be configured as a disposable injection device with the container 100 readily assembled therein. Alternatively, the injection device 1 may be configured as a reusable device. Here, the cartridge holder 21 can be disconnected from the body 22 to replace or to exchange a container 100.

The cartridge holder 21 as illustrated in FIG. 2 comprises a window 25 to allow visual inspection of the container 100 located therein. Near a distal end the cartridge holder 21 comprises a socket 31 having an outer threaded section 32. The socket 31 is configured to support an injection needle 40. The injection needle 40 typically comprises a double-tipped hollow cannula having a proximal end and a distal end. The injection needle 40 typically comprises a needle hub 41 with an inside threaded portion for releasable connection with the threaded section 132. The needle hub 41 comprises a bottom section and a sidewall section forming a cup-shaped receptacle configured to receive the threaded socket 31 of the cartridge holder 21. The sidewall section comprises the inner threaded section that mates with the outer threaded section 32 of the socket 31. A distal end face of the cartridge holder 21 comprises a through opening 23 through which the proximally protruding portion of the needle 40 can extend into the interior of the cartridge holder 21 and hence into the interior of the cartridge or container 100 when the injection needle 40 is attached to the cartridge holder 21 and when the container 100 is arranged in the cartridge holder 21.

The container 100 is arranged inside the cartridge holder 21. It is positionally fixed inside the cartridge holder 21. The container 100 comprises an elongated and tubular-shaped body 101. The body 101 may comprise a vitreous body. The body 101 may be made of glass. The body 101 may be translucent or transparent in order to allow visual inspection of the content of the container 100. The elongated body 101 extends along a longitudinal direction (z). The body 101 comprises the distal end 103 and an oppositely located proximal end 104.

With the distal end 103 the body 101 is arranged near or at the distal end of the cartridge holder 21. The distal end 103 of the body 101 comprises a narrowing shoulder portion 107 extending into a diameter reduced neck portion 105. The radially narrowing shoulder portion 107 is configured to abut or to engage axially with a correspondingly-shaped shoulder section of the cartridge holder 21. The shoulder portion 107 is located close to the distal end 103 of the cartridge or container 100.

At the far distal end the neck portion 105 extends into a radially widening head portion 105a. At the head portion 105a there is provided a seal 206, e.g. in form of a pierceable sealing disc. This seal 206 may comprise a pierceable rubber septum that is fixed to the head portion 105a and hence to the distal end 103 of the body 101 by means of a ferrule 108 or crimped metal cap. The ferrule 108 may comprise a crimped aluminium cap. The seal 206 may form or belong to an outlet 109 of the container 100 at the distal end 103 of the elongated body 101.

The injection device 100 may be further equipped with a drive mechanism 14 comprising a plunger or a piston rod 11. The drive mechanism 14 may be further equipped with a trigger 18 by way of which a dispensing action of the injection device 1 can be triggered or controlled. Optionally, the injection device 1 and the drive mechanism 14 comprise a dose dial 16 by way of which a size of a dose to be dispensed can be individually set or by way of which the injection device 1 can be deployed or prepared for a subsequent dispensing procedure.

Optionally and as illustrated in FIG. 1 the body 22 of the housing 20 may be provided with a dose size indicating window 26. In the window 26 the size of a dose actually set can be visually displayed thus informing the user of the amount of the medicament to be dispensed during a subsequent dispensing procedure.

As further illustrated in FIG. 1 the injection needle 40 may be provided with an inner needle cap 27 configured to cover the distal end of the injection needle 40. The injection needle and/or the needle hub 41 may be further covered by an outer needle cap 28. If not in use the injection needle 40 should be detached from the distal end of the cartridge holder 21. Then, the cartridge holder 21 can and should be covered by a protective cap 24. The protective cap 124 is configured to releasably engage with at least one of the cartridge holder 21 and the body 22. Prior to assemble the injection needle 40 to the cartridge holder 21 the protective cap 24 has to be detached from the housing 20.

The above described interaction of the container 100 with a pen type injection device 1 as illustrated in FIGS. 1-2 is only exemplary. The general working principle of the container does not require interaction with a pen type injection device 1. Generally, the container 100 can be implemented or may be used as a manually operated syringe or as a container for an infusion device.

Figure 3:
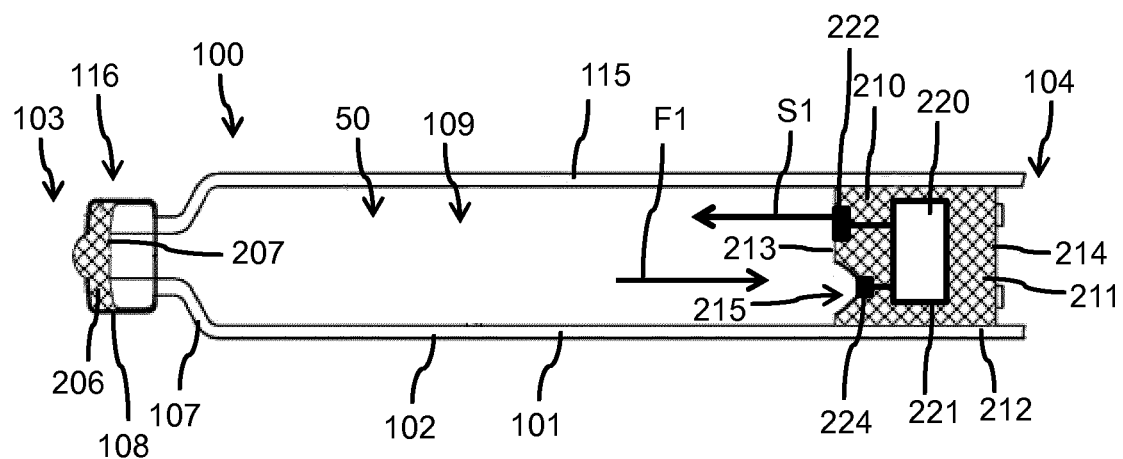
FIG. 3 shows a longitudinal cross-section through an example of the container.

The container 100 as illustrated in FIG. 3 comprises a tubular-shaped elongated body 101 having a tubular-shaped sidewall 102. At the distal end 103 the container 100 comprises an outlet 116. The outlet 116 is sealed by the pierceable seal 206. Near a proximal end 104 that is opposite to the distal end 103 the container 100 comprises a bung 210 or a piston. The bung 210 is arranged inside the tubular-shaped sidewall 101 of the container 100. The bung 210 is sealingly engaged with an inside section of the sidewall 102.

The bung 210 comprises an outer tubular shaped sidewall 212 in frictional engagement with an inside of the sidewall 102 of the container 100.

The cross-section or diameter of the bung 210 matches with the respective cross-section or diameter of the body 101 and of its sidewall 102. The bung 210 comprises a body 211. The bung 210 comprises a distal face 213 facing towards the outlet 116 and hence towards the pierceable seal 206. Opposite to the distal face 213 the bung 210 comprises a proximal face 214. The proximal face 214 serves as a thrust receiving face of the bung 210. The proximal face 214 may get in axial or longitudinal abutment with the piston rod 11 of the drive mechanism 14 of an injection device 1 as illustrated in FIGS. 1 and 2.

In this way, the bung 210 can be urged or pushed in distal direction 2 so as to expel a predefined amount of the injectable medicament 50 from an interior volume 109 of the container 100. The interior volume 109 is confined in circumferential direction or in radial direction by the sidewall 102 of the container 100. In distal direction 2 the interior volume 109 is confined by the outlet 116. The interior volume 109 may be confined in distal direction 2 by the pierceable seal 206. In proximal direction 3 the interior volume 109 is confined by the bung 210. In particular, the interior volume 109 is confined by the distal face 213 of the bung 210.

The interior volume 109 defines the amount of injectable medicament 50 accommodated inside the container 100. During use of the container 100 and as the injectable medicament 50 is expelled from the interior of the container 100 the size of the interior volume 109 decreases as the bung 210 is driven in distal direction 2 towards the outlet 116. In order to measure or to determine the size of the interior volume 109 the bung 210 comprises a measuring arrangement 220. The measuring arrangement 220 is arranged in or on the bung 210. The measuring arrangement 220 may be encapsulated entirely inside a body 211 of the bung 210. The measuring arrangement 220 may be located inside the bung 210 at a predefined non-zero distance from any of the distal face 213, the proximal face 214 and the outer sidewall 212 of the bung 210.

In one example the measuring arrangement 220 comprises a housing 221. The measuring arrangement 220 or at least one component thereof may be alternatively arranged inside the bung 210 and outside the housing 221 so that the measuring arrangement 220 or at least one component thereof is arranged flush with an outer surface of the body 211 of the bung 210. For instance, the measuring arrangement 220 may flush with the distal face 213 or with the proximal face 214. The measuring arrangement 220 or components thereof may also protrude from at least one of the distal face 213 and the proximal face 214.

Figure 4:
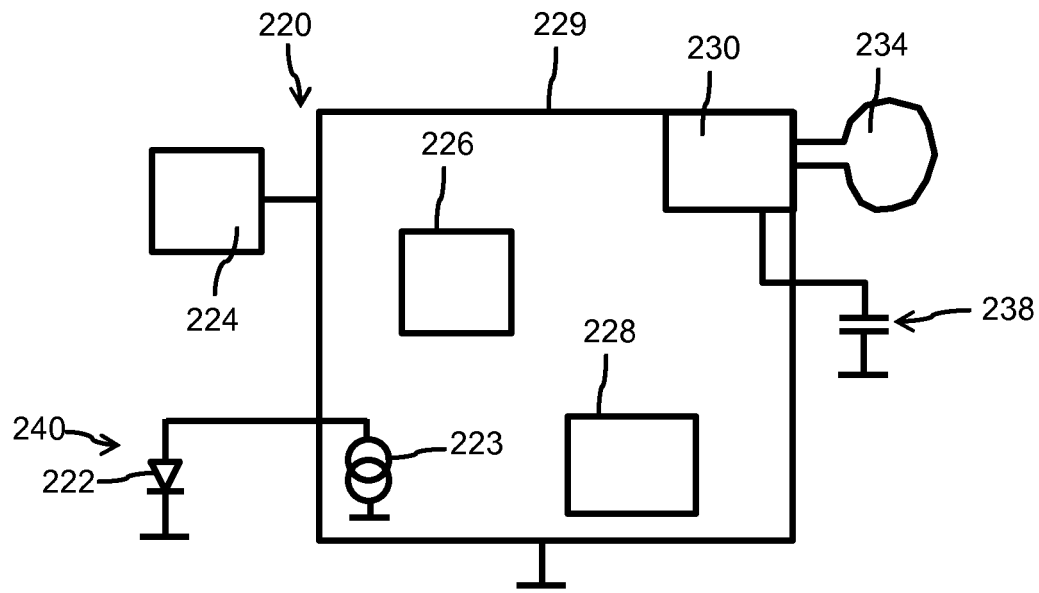
FIG. 4 is a block diagram of the measuring arrangement of FIG. 3.

One example of the measuring arrangement 220 with its components is schematically illustrated in more detail in FIG. 4. The measuring arrangement 220 comprises a signal generator 222 that is configured to emit an electromagnetic measurement signal S1 into or through the interior volume 109. The measurement signal S1 is an electromagnetic signal. The electromagnetic signal may comprise or represent an optical signal. It may comprise at least one of a light beam and a light pulse.

The measuring arrangement 220 further comprises a signal receiver 224 that is configured to detect an electromagnetic feedback signal F1. The electromagnetic feedback signal F1 is indicative of an interaction of the measurement signal with at least one of the sidewall 102, the outlet 116 and the interior volume 109. By emitting the measurement signal S1 into the interior volume 109 a respective feedback signal F1 is generated that is directly indicative of the interaction of the measurement signal S1 with at least one of the sidewall 102, the outlet 116, the pierceable seal 206 or the interior volume 109. On the basis of the detected feedback signal F1 alone or on the basis of a comparison of the feedback signal F1 with the measurement signal S1 a precise determination of the size of the interior volume 109 can be provided. Based on the feedback signal F1 alone and/or based on the respective measurement signal S1 the longitudinal position of the bung 210 relative to the body 101 of the container 100 can be determined or measured. From this, a momentary size of the interior volume 109 can be derived.

The block diagram of FIG. 4 shows one example of a measuring arrangement 220. The measuring arrangement 220 may comprise a housing 221 that provides and enables an encapsulation of the measuring arrangement 220 in the inside of the body 211 of the bung 210. The measuring arrangement 220 comprises a processor 226. The processor 226 is a microprocessor, e.g. in form of a microcontroller or in form of an application-specific integrated circuit (ASIC). The measuring arrangement 220 may comprise a PCB 229. In the example of FIG. 4 the signal generator 222 of the measuring arrangement 220 comprises a light source 240, such as a light emitting diode (LED).

Upon manufacturing, assembly or filling of the container 100 with the injectable medicament 50 a measurable geometric property of the container 100 can be individually determined.

The measuring arrangement 220 may further comprise a communication interface 230 that is configured to exchange data with an external electronic device 400 as illustrated in FIG. 2. The external electronic device 400 typically comprises a processor 402, a data storage 404 and a communication interface 406. The communication interface 406 is configured to communicate and to exchange data with the communication interface 230 of the measuring arrangement 220. Typically, the communication interface 230 as well as the communication interface 406 is or are configured for wireless data transmission. The communication interface 230 and/or the communication interface 406 might be configured to communicate via RF electromagnetic signals. The communication interfaces 230, 406 may be for instance configured for wireless communication in accordance to the Wi-Fi standard (IEEE802.11), RFID or NFC communication or Bluetooth communication protocols and standards.

The measuring arrangement 220 may further comprise an antenna 234 in order to enable wireless data transmission between the measuring arrangement 220 and an external electronic device 400. The antenna 234 may be further configured to withdraw or to harvest electromagnetic energy from an external electromagnetic field EM, e.g. from a radio-frequency field (RF). It is generally conceivable, that the measuring arrangement 220 is entirely driven by electromagnetic energy withdrawn from an external electromagnetic field EM. Alternatively or additionally it is conceivable that the measuring arrangement 220 comprises an electric energy storage 238, e.g. implemented as a rechargeable battery. The electric energy storage 238 may be connected to the antenna 234 as well as to the processor 226. The electric energy storage 238 can be recharged by electric energy withdrawn from the external electromagnetic field EM through the antenna 234.

It is generally conceivable, that the processor 226 is limited to transfer electric signals obtainable from a signal receiver 224 via the communication interface 230 to the external electronic device 400. In this way, computational power of the measuring arrangement 220 as well as electric power consumption could be reduced to a minimum. The processing of signals obtainable from the signal receiver 224 may be entirely conducted by the processor 402 of the external electronic device 400. Hence, a software application implemented in the external electronic device 400 may provide a calculation of the size of the interior volume 109 and may be configured to determine the momentary filling level of the container 100.

With another example the processor 226 may be configured to determine or to calculate the size of the interior volume 109 based on the signals received by the signal receiver 224. Pre-processed signals or unprocessed signals of the receiver 224 and/or processed data derived from a detected feedback signal and/or from an emitted measurement signal may be also stored in the data storage 228. Communication and transfer of data between the measuring arrangement 220 and the external electronic device 400 may be thus limited to the size of the interior volume and/or to the momentary longitudinal position of the bung 210 relative to the body 101 of the container 100.

Furthermore, it is conceivable, that the data storage 228 is configured to store numerous size informations regarding the interior volume or regarding the longitudinal position of the bung 210. The data storage 228 may be configured to store a dosing history. The data storage 228 may be configured to store data derived from the measurement signal S1 and/or from the feedback signal F1 together with a timestamp. In this way a dosing history of the container 100 may be stored inside the bung 210.

The signal generator 222 of the example according to FIGS. 3 and 4 is configured to emit an optical, hence an electromagnetic measurement signal S1. The electromagnetic measurement signal S1 is generated and emitted by the signal generator 222 in such a way that the optical measurement signal S1 propagates into the interior volume 109 of the container 100. The optical measurement signal S1 is interacting with at least one of the sidewall 102, the outlet 116 or the interior volume 109, hence with the injectable medicament 50. The optical measurement signal S1 may be reflected, diffracted, and/or absorbed by at least one of the sidewall 102, the outlet 116, the interior volume 109 and the injectable medicament 50 located therein. In reaction to such interaction there is generated or there emerges an electromagnetic feedback signal F1 that is detectable by the signal receiver 224.

In one example the signal generator 222 comprises a light source 240 to emit a light beam or a light pulse into the interior volume 109. The signal receiver 224 may comprise a photodiode or a light detector, e.g. in form of a charge coupled device to detect the optical feedback signal F1. In one example the signal receiver comprises an optical Time-of-flight (TOF) detector 242. The optical feedback signal F1 may be a reflection of the optical measurement signal S1. As an alternative it may be a portion of the optical measurement signal S1 scattered on or by at least one of the sidewall 102, the outlet 116, the interior volume 109 or the injectable medicament 50.

In one example the signal receiver 224 is a time of flight detector 242. For this, both the signal generator 222, e.g. in form of an ultra-fast LED and the signal receiver 224 are connected to the processor 226. The signal generator 222 may be pulsed by a comparatively fast current source 223 controlled and triggered by the processor 226. The signal receiver 224, e.g. in form of an extremely or comparatively fast TOF sensor or photodiode receives the electromagnetic or optical feedback signals F1 that are reflected from the interior volume 109, from the outlet 116 or from the sidewall 102 of the body 101 of the container. Typically, several light pulses or a sequence of light pulses is generated and emitted by the signal generator 222.

The detected reflected light pulses forming the optical feedback signal F1 are detected by the signal receiver 224. From a phase shift and/or from a time delay between the emission of optical measurement signals S1 and the detection of respective optical feedback signals F1 the processor 226 is able to calculate or to determine a runtime or a distance between the signal generator 222, a reflected structure of the container and the signal receiver 224. Typically, an inside surface 207 or the proximal surface of the pierceable seal 206 may comprise a reflective surface. In this way, optical measurement signals S1 propagating through the interior volume 109 are reflected at the proximal surface 207 and are returned as optical feedback signals F1 to the signal receiver 224. Also here and upon manufacturing, upon assembly or upon filling of the container 100 a respective calibration procedure may be conducted.

For instance, the signal generator 222 is configured to generate and to emit at least one or several light pulses into the interior volume 109 at a first point of time t1 and the signal receiver 224 is configured to detect at least one or several reflected light pulses. The signal receiver 224 is particularly configured to detect light pulses previously emitted by the signal generator 222 and reflected by at least one of the sidewall 102, the outlet 116 and the proximal surface 207 of the pierceable seal 206. The signal receiver 224 is configured to detect or to determine a second point of time t2 at which reflected light pulses are detected. A time interval between the first point of time t1 and the second point of time t2 is indicative of a time delay required by the emitted light to propagate from the signal generator 224 to the signal receiver 224. Typically, both the signal generator 222 and the signal receiver 224 are connected to the processor 226 and are driven or triggered by the processor 226. The optical signal generator 222 and/or the optical signal receiver 224 may be entirely enclosed or embedded inside the body 211 of the bung 210. For this the material of the body 211 of the bung 210 may be substantially translucent for the wavelength of the electromagnetic measurement signal and the respective electromagnetic feedback signal. Otherwise and with a non-translucent or non-transparent material of the bung 210 the optical signal generator 222 and the optical signal receiver 224 may be located at the distal face 213 of the body 211 of the bung 210.

As illustrated in FIG. 3 at least one of the signal generator 222 and the signal receiver 224 may be located in a recess 215 of the distal face 213 of the bung 210. As illustrated in FIG. 3, the signal generator 222, e.g. in form of an LED is located in the recess 215. The optical signal receiver 224 is flush with the distal face 213 of the body 211 of the bung 210. In this way it is guaranteed that even in a distal most position of the bung 110 there remains at least a minimum propagation distance for the optical measurement signal S1 and the optical feedback signal F1 which is required to enable a measurement of the distance between the bung 210 and the outlet 116.

The recessed arrangement of the optical signal generator 222 is also beneficial to avoid a direct illumination of the optical signal receiver 224 by electromagnetic or optical measurement signals S1. The recessed arrangement of at least one of the signal generator 222 and the signal receiver 224 provides a kind of a screening for the optical signal receiver 224. In this way it can be provided that only optical feedback signals F1 reflected from at least one of the sidewall 102, the outlet 116 or the proximal surface 207 impinge on the signal receiver 224.

Figure 5:
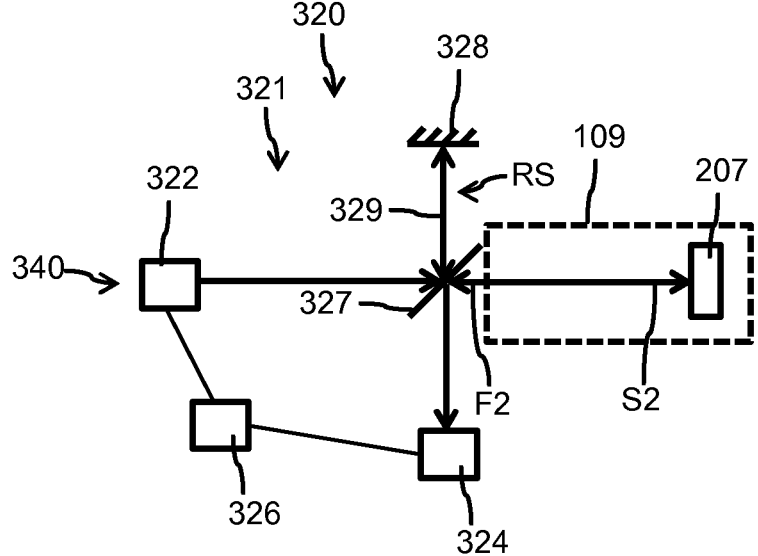
FIG. 5 is a further block diagram of an alternative measurement arrangement comprising an optical interferometer.

In another example as indicated in FIG. 5 the measuring arrangement 320 comprises an optical interferometer 321. The optical interferometer 321 comprises an optical signal generator 322 comprising a light source 340, e.g. an LED configured to generate a light beam or a light pulse of a sufficient coherence length. The optical interferometer 321 further comprises a processor 326 and an optical signal receiver 324. The optical signal receiver may comprise a photodiode or an array of photodiodes or charge coupled pixels.

The optical interferometer 321 is embedded inside the bung 210 as illustrated in FIG. 3. The optical interferometer 321 comprises a beam splitter 327 and a reflector 228. A light beam produced by the optical signal generator 322 propagates to the beam splitter 327. There, the light beam is split into a signal beam S2 and into a reference beam RS. The reference beam RS is reflected towards the reflector 328. At the reflector 328 the reference beam RS is reflected towards the beam splitter 327. The signal beam S2 representing the optical measurement signal propagates into the interior volume 109 of the container 100. There, it is reflected at a reflective structure, e.g. at the inside surface 207 of the pierceable seal 206. In one example the beam splitter 327, the optical signal receiver 224 and the reflector 328 are all implemented and arranged inside the bung 210.

The beam splitter 327 may be arranged in the distal face 213 of the bung 210. It may be arranged in a recess 215 of the distal face 213 as described in connection with FIG. 3. The optical feedback signal F2 reflected from the surface 207 is redirected towards the beam splitter 327. There, the reflected reference beam RS and the optical feedback signal F2 recombine and co-propagate towards the optical signal receiver 324. As a consequence, an interference pattern evolves on the optical signal receiver 324. As the distance between the beam splitter 327 and the surface 207 changes because of a movement of the bung 210 towards the outlet 116 the structure of the interference pattern changes. The change of the structure of the interference pattern is directly indicative of the distance the bung 210 is displaced relative to the body 101 of the container 100.

The distance between the beam splitter 327 and the reflector 328 is constant. The reference beam RS may propagate through an optical fiber 329 also enabling to realize a comparatively long optical path length between the beam splitter 327 and the reflector 328 inside the bung 210.

In the flowchart of FIG. 6 various method steps of the method of determining the size of the interior volume 109 are illustrated. In an initial step 500 the container 100 is assembled. Here, the bung 210 is inserted into the body 101 of the container 100. Thereafter the outlet 116 may be sealed, e.g. by arranging the pierceable seal 206 on the head portion 105a of the container 100. In a subsequent step 502 an initial measurement is conducted. Here, the signal generator 222, 322 is triggered to emit at least one measurement signal S1, S2 into or through the interior volume 109. At least one or a sequence of feedback signals F1, F2 is or are detected by the signal receiver 224, 324. Thereafter in a subsequent step 504, the measured signals are calibrated. Hence, the results of the initial measurement are assigned with the actual size of the interior volume 109 that is determined or predetermined during the assembly process.

In step 506 a calibration is stored in the data storage 228. Later on and during use of the container, e.g. in an injection device the measuring arrangement 220, 320 may be triggered to conduct a respective measurement and to emit at least a measurement signal S1, S2 into or through the interior volume 109 in step 508.

In a subsequent step 510 at least one or a series of feedback signals F1, F2 is or are received by the signal receiver 224, 324. From the received signal(s), in particular from a time delay between submission of the electromagnetic measurement signal and receiving of a reflected electromagnetic feedback signal and with knowledge of the refractive index of the medium through which the electromagnetic signals propagate an optical path length between the signal generator and the signal receiver can be calculated on the basis of the known velocity of the electromagnetic radiation. From the time delay an axial distance between the distal face 213 of the bung 210 and e.g. the proximal surface 207 of the pierceable seal 206 can be calculated in step 512. Having knowledge of the diameter and/or of the geometric cross-section of the container 100 the size of the interior volume 209 and the amount of medicament left inside the container 100 can be precisely calculated.

It should be noted, that various modifications to the flowchart as described above with respect to FIG. 6 are conceivable in accordance to the functionality of the various examples of the measuring arrangement and its interaction with, e.g. an external electronic device 400.

Two further examples of drug containers 100 are illustrated in FIG. 7 and FIG. 8. There, the bung 210 comprises a rather large recessed portion 215. A distal face 213 of the bung 210 is in contact with the liquid drug 50. The recessed portion 215 is open towards the interior volume 109. As illustrated in FIG. 7 the signal receiver 224 is located on a bottom of the recessed portion 215. The axial length of the recessed portion 215 is larger than 30% of the total axial length L of the bung 210. It may be larger than 50% of the total axial length L of the bung 210. In other examples, the axial length or axial depth of the recessed portion 215 may be larger than 60%, larger than 75% or even larger than or equal to 80% of the total axial length L of the bung 210.

In this way the optical path length for electromagnetic radiation emitted by the signal generator, reflected at the distal end 103 and detected by the signal receiver 224 can be substantially prolonged compared to the example as illustrated in FIG. 3. This is of particular benefit when the bung 210 should be located rather close to the distal end 103 of the container 100. The prolongation of the optical path length is beneficial for a time-of-flight measurement of electromagnetic radiation emitted by the signal generator 222 and received through the signal receiver 224. The axial length of the recessed portion 215 provides a well-defined runtime offset for at least one of the electromagnetic signals S1, F1.

Apart from this geometric variation the bung 210 of FIG. 7 is rather identical or highly similar to the bung 210 as described with regard to FIG. 3. Insofar all features and properties of the bung 210 as described in connection with FIG. 3 are equally valid for the bung 210 as described in FIGS. 7 and 8.

As an alternative to the illustration of FIG. 7 the recessed portion 215 may accommodate the signal generator 222, whereas the signal receiver 224 is located at the distal face 213 of the bung 210. At least one of the signal generator 222 and the signal receiver 224 is located on the bottom of the recessed portion 215.

With the example of FIG. 8 the recessed portion 215 is divided into a first recessed section 215a and a second recessed section 215b. In the first recessed section 215a there is located the signal receiver 224. In the second recessed section 215b there is located the signal generator 222. The two recessed portions 215a, 215b are separated by a separator 216. The separator 216 may be formed by a partition wall protruding axially in distal direction from a bottom of the recessed portion 215. The first recessed section 215a and the second recessed section 215b are separated in radial direction. They may be located at the same or at different axial positions with regard to the axial elongation of the bung 210.

Also here, the total axial length of the recessed portion 215 can be larger than 30%, larger than 50%, of the land 60%, larger than 75% or even larger than or equal to 80% of the total axial length L of the bung 210. The axial length of the separator 216 may be smaller than the axial length of the recessed portion 215. Insofar, a free and distally extending end of the separator 216 facing away from the bottom of the recessed portion 215 may be proximally recessed compared to the distal face 213 of the bung 210. With other examples the total axial length of the separated 260 may be substantially equal to the axial length of the recessed portion 215 or of any of its recessed sections 215a, 215b.

With any of the examples as illustrated in the figures and/or as described above the recessed portion 215 may be either filled by the liquid medicament 50 or it may be filled with a transparent filling material 217. For instance, the recessed portion 215 may be filled with a transparent polymer. The filling material 217 may comprise at least one of COC, PA, PP, PE, POM, PS, ABS, COP or mixtures thereof. Filling the recessed portion 215 by a filling material 217 is beneficial to maintain the mechanical stability of the bung 210 and to provide a sufficient sealing functionality of the bung 210 with regard to the sidewall 212.

LIST OF REFERENCE NUMBERS 1 injection device
2 distal direction
3 proximal direction
11 piston rod
14 drive mechanism
16 dose dial
18 trigger
20 housing
21 cartridge holder
22 body
23 through opening
24 cap
25 window
26 window
27 inner needle cap
28 outer needle cap
31 socket
32 thread
40 injection needle
41 needle hub
50 medicament
100 container
101 body
102 sidewall
103 distal end
104 proximal end
105 neck portion
105a head portion
107 shoulder portion
108 ferrule
109 interior volume
115 sidewall
116 outlet 206 pierceable seal
207 surface
209 interior volume
210 bung
211 body
212 sidewall
213 distal face
214 proximal face
215 recessed portion
215a recessed section
215b recessed section
216 separator
217 filling material
220 measuring arrangement
221 housing
222 signal generator
223 current source
224 signal receiver
226 processor
228 data storage
229 printed circuit board
230 communication interface
234 antenna
238 electric energy storage
240 light source
242 TOF detector
320 measuring arrangement
321 optical interferometer
322 signal generator
324 signal receiver
326 processor
327 beam splitter
328 reflector
329 optical fiber
340 light source
400 external electronic device
402 processor
404 data storage
406 communication interface

The invention claimed is:

1. A container for an injectable medicament, the container comprising:
an elongated body having a tubular-shaped sidewall extending along a longitudinal axis and having a distal end and a proximal end,
an outlet at the distal end,
a bung arranged inside the elongated body, sealingly engaged with the tubular-shaped sidewall, and slidable along the longitudinal axis relative to the tubular-shaped sidewall,
an interior volume to receive the injectable medicament and being confined by the tubular-shaped sidewall, by the outlet, and by the bung,
a measuring arrangement arranged in or on the bung, the measuring arrangement comprising:
an optical interferometer comprising
an optical signal generator configured to emit an optical measurement signal into or through the interior volume, and
an optical signal receiver configured to detect an optical feedback signal indicative of an interaction of the optical measurement signal with at least one of the tubular-shaped sidewall, the outlet, or the interior volume, and
a processor configured to determine a position of the bung relative to the elongated body of the container based on the optical measurement signal and the optical feedback signal.

2. The container according to claim 1, wherein the processor is configured to determine a size of the interior volume based on the determined position of the bung relative to the elongated body of the container.

3. The container according to claim 1, wherein the processor is connected to the optical signal generator, wherein the processor is configured to trigger the emission of the optical measurement signal, and wherein the processor is configured to determine a size of the interior volume based on a comparison of the optical measurement signal with the optical feedback signal.

4. The container according to claim 1, wherein the measuring arrangement comprises a data storage configured to store at least one of (i) an initial size of the interior volume and (ii) the optical feedback signal, and the container comprises a communication interface configured to exchange data with an external electronic device.

5. The container according to claim 1, further comprising:
an antenna configured to withdraw electric energy from a surrounding electromagnetic field, and
an electric energy storage connected to the antenna and configured to store the withdrawn electric energy from the surrounding electromagnetic field.

6. The container according to claim 1, wherein the optical signal generator comprises a light source configured to emit the optical measurement signal towards the outlet.

7. The container according to claim 6, wherein the optical signal receiver comprises a detector or a camera configured to detect the optical measurement signal reflected from the outlet as the optical feedback signal.

8. The container according to claim 7, wherein the optical interferometer is configured to determine a distance between the outlet and the bung based on an optical phase shift between the optical feedback signal and an optical reference signal.

9. The container according to claim 8, wherein the optical interferometer comprises an optical fiber forming a reference path for the optical reference signal.

10. The container according to claim 6, wherein the optical signal generator is configured to generate and emit at least one light pulse into the interior volume at a first point of time, wherein the optical signal receiver is configured to detect at least one reflected light pulse at a second point of time, and wherein at least one of the processor or the optical signal receiver is configured to determine a time interval between the first point of time and the second point of time.

11. The container according to claim 6, wherein at least one of the optical signal generator or the optical signal receiver is arranged in a recessed portion of a distal face of the bung.

12. The container according to claim 11, wherein the recessed portion comprises a first recessed section and a second recessed section, the optical signal generator being located in the first recessed section, and the optical signal receiver being located in the second recessed section.

13. The container according to claim 1, wherein the optical interferometer comprises a beam splitter and a reflector, wherein the beam splitter is disposed inside the bung or in a recess of a distal face of the bung.

14. The container according to claim 13, wherein the optical interferometer is configured to emit the optical measurement signal into or through the interior volume by:

splitting, by the beam splitter, a light beam generated by the optical signal generator into a signal beam and a reference beam, and emitting the signal beam into the interior volume of the container, the emitted signal beam representing the optical measurement signal.

15. The container according to claim 14, wherein the optical interferometer is configured to:

combine the reference beam and the optical feedback signal into a combined signal, receive the combined signal at the optical signal receiver, and detect, by the optical signal receiver, an interference pattern or an optical phase shift of the combined signal.

16. The container according to claim 15, wherein the processor is configured to determine the position of the bung relative to the elongated body of the container based on the interference pattern or the optical phase shift.

17. The container according to claim 15, wherein the optical interferometer comprises an optical fiber disposed inside the bung, the optical fiber forming a reference path for the reference beam.

18. A method of determining a size of an interior volume of a container, the container comprising an elongated body having a tubular-shaped sidewall extending along a longitudinal axis and having a distal end and a proximal end, an outlet at the distal end, a bung arranged inside the elongated body, sealingly engaged with the tubular-shaped sidewall, and slidable along the longitudinal axis relative to the tubular-shaped sidewall, the interior volume to receive an injectable medicament and being confined by the tubular-shaped sidewall, by the outlet, and by the bung, a measuring arrangement arranged in or on the bung, the method comprising:

generating and emitting an optical measurement signal from an optical signal generator of an optical interferometer of the measuring arrangement into or through the interior volume of the container, detecting, by an optical signal receiver of the optical interferometer, an optical feedback signal indicative of an interaction of the optical measurement signal with at least one of the tubular-shaped sidewall, the outlet, or the interior volume of the container, and determining, by a processor of the measuring arrangement, the size of the interior volume based on the optical measurement signal and the optical feedback signal.

19. The method of claim 18, further comprising triggering the emission of the optical measurement signal and determining the size of the interior volume based on a comparison of the optical measurement signal with the optical feedback signal.

20. The method of claim 18, wherein determining the size of the interior volume based on the optical feedback signal comprises determining a time or time delay at which the optical feedback signal is detected.

21. The method of claim 18, wherein determining the size of the interior volume based on the optical feedback signal comprises determining a phase shift between the optical feedback signal and a reference signal.

22. The method of claim 18, wherein determining the size of the interior volume based on the optical feedback signal comprises monitoring and processing a temporal variation of the optical feedback signal or a series of optical feedback signals.

* * * * *